United States Patent [19]

Müller

[11] Patent Number: 4,721,137

[45] Date of Patent: Jan. 26, 1988

[54] APPARATUS FOR WITHDRAWING LIQUID FROM CLOSED RECEPTACLE

[75] Inventor: Paul Müller, Steinhausen, Switzerland

[73] Assignee: Kontron Holding A.G., Zurich, Switzerland

[21] Appl. No.: 916,332

[22] Filed: Oct. 7, 1986

[30] Foreign Application Priority Data

Oct. 9, 1985 [CH] Switzerland ............... 4356/85

[51] Int. Cl.⁴ .................................. B65B 3/04
[52] U.S. Cl. ........................ 141/65; 141/330; 141/276
[58] Field of Search ............. 141/65, 66, 329, 330, 141/19, 250–284

[56] References Cited

U.S. PATENT DOCUMENTS 512,147  4/1955  Taunton et al. .................. 141/65

Primary Examiner—Houston S. Bell, Jr.
Attorney, Agent, or Firm—Jon S. Saxe; Bernard S. Leon; Richard J. Mazza

[57] ABSTRACT

An apparatus for withdrawing liquid from a receptacle which is closed with a penetrable cover, which comprises a puncturing tool for creating an aperture in the receptacle cover, a cannula for entering the receptacle through the aperture and withdrawing liquid from the receptacle, a holding arm to which the puncturing tool and cannula are affixed in parallel and at a certain distance apart, and a motor drive for effecting horizontal and vertical movements of the holding arm relative to the covered receptacle to align, lower and raise the puncturing tool and cannula in succession through the cover.

3 Claims, 2 Drawing Figures

APPARATUS FOR WITHDRAWING LIQUID FROM CLOSED RECEPTACLE

BACKGROUND OF THE INVENTION

The invention relates to an apparatus for withdrawing liquid from a receptacle closed by a cover.

To ensure sterility and to reduce difficulties connected with solvent evaporation, reagents and samples for automatic analysis systems are often provided in receptacles which are closed by a resilient septum or by a plastic cover. Withdrawal of the liquid contents of the receptacle is accomplished by means of a withdrawal cannula which is connected by way of flexible piping to a pump and which pierces the cover in order to dip into the body of liquid.

To reduce the risk of contamination, analysis samples are often dispatched or delivered in receptacles of this kind, and specimens are withdrawn by means of a withdrawal apparatus with the use of an appropriate cannula.

To ensure that the resilient cover, which is often in the form of a rubber diaphragm, is punctured neatly the cannula must have a special high-precision sharpening and so is relatively expensive. Even then, it is often impossible to prevent the cannula from becoming blocked by dislodged pieces of the diaphragm. Further, the force required to puncture the diaphragm is relatively high despite the special sharpening of the cannula tip, and so the pivot arms and bearings experience elevated forces. Yet another disadvantage is that the diaphragm engages sealingly with the cannula so that when liquid is removed a negative pressure is generated in the receptacle which has disadvantageous consequences; for example, the negative pressure may impair sampling accuracy when sample quantities are small.

It is an object of the present invention to disclose an improved apparatus designed to avoid the above-mentioned disadvantages.

DESCRIPTION OF THE INVENTION

According to the present invention, in an apparatus for withdrawing liquid a puncturing tool is disposed adjacent to and spaced apart from the withdrawal cannula and means are provided for so controlling the relative mechanical movements between the cannula holder and the receptacle such that in a first descent of the cannula holder the puncturing tool alone (not the cannula) is aligned with and pierces the cover of the receptacle, after which a relative lateral movement through a distance corresponding to the distance between the puncturing tool and the cannula ensues, after which in a second descent of the cannula holder the cannula alone (not the puncturing tool) is aligned with and penetrates through the previously made puncture or channel in the cover.

BRIEF DESCRIPTION OF THE DRAWINGS

An embodiment of the invention will be described hereinafter with reference to the accompanying drawings, wherein.

DETAILED DESCRIPTION OF THE DRAWINGS

Figure 1:
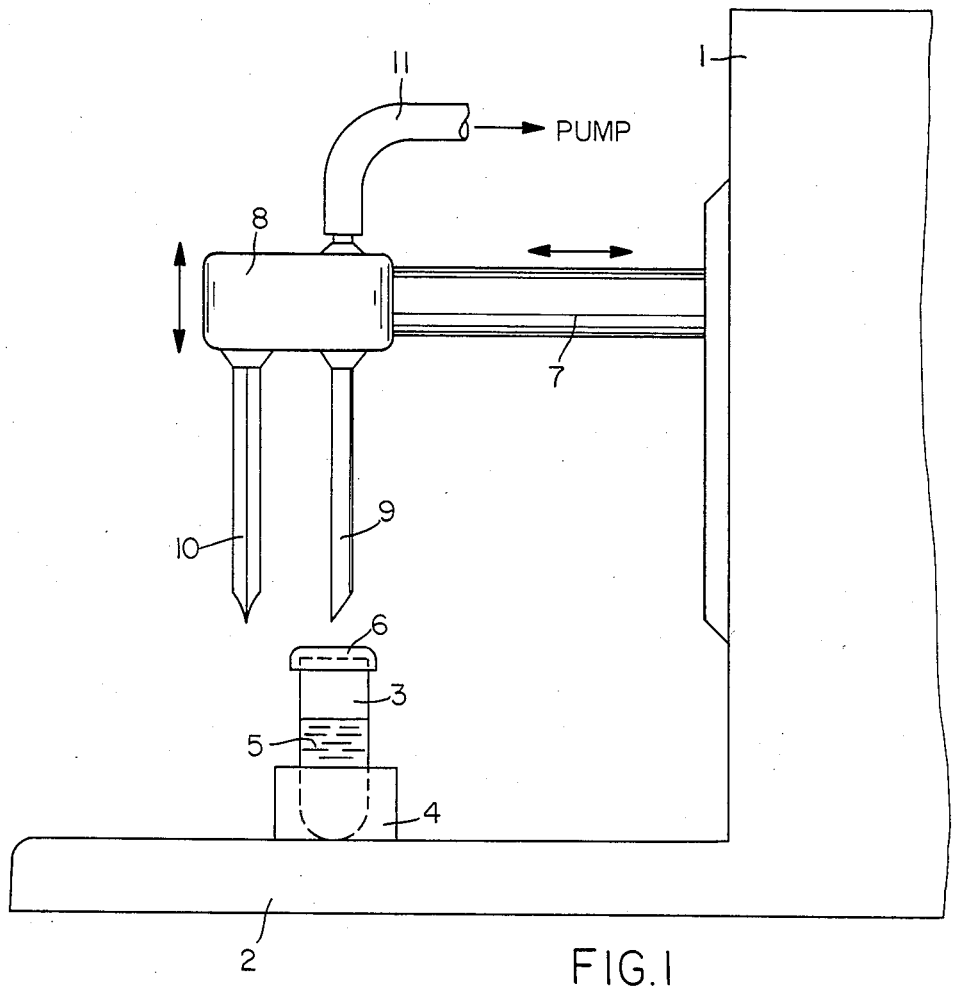
FIG. 1 is a diagrammatic view of a sampling apparatus, in accordance with the present invention

As shown in FIG. 1, a pipetting device in accordance with this invention has a casing 1 which has a table-like bottom part or base 2. A liquid receptacle 3, from which it is required to pipette a portion of liquid, is placed on base 2. The receptacle 3 is mounted on frame 4, which is either stationary on base 2 or capable of being moved thereon by a conveyor (not shown).

The receptacle 3 contains a liquid 5, such as a reagent, or test specimen, or the like, and is closed by a resilient diaphragm 6 made, for example, of rubber, plastic, or the like.

A pipetting head 8, which functions as a holding means, is disposed on arm 7 on the top part of casing 1 and has a downwardly extending pipetting needle or cannula 9 and, disposed parallel to and at a distance therefrom, a puncturing tool 7. A drive (not shown) is adapted to move arm 7 as indicated by arrows, i.e., horizontally and vertically. The drive mechanisms enabling pipetting apparatuses to perform movements of this kind are known in the art and need not, therefore, be described here in detail.

The needle 9 is a cannula which extends through head 8 and communicates at the top with a flexible hose 11 which extends to a pump.

Figure 2:
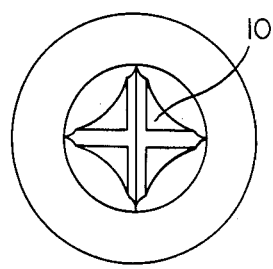
FIG. 2 is an inverted plan view of a portion of the apparatus of FIG. 1.

The puncturing tool 10 is rigidly secured to the underside of head 8. Puncturing tool 10 is in cross-section substantially cruciform and has a tip which has been ground to a sharp point. FIG. 2 is an inverted plan view of tool 10.

In an actual system where not only one receptacle but a multiplicity of receptacles arranged in a matrix-shaped array are presented to the apparatus, it will be understood that an appropriate number of cannulas and puncturing tools are associated with the pipetting head.

The drive (not shown) for arm 7 carries out the following mechanical cycle for each newly arrived receptacle:

I. The puncturing tool 10 is moved by an appropriate lateral movement into a position in which it is aligned and substantially concentric with the receptacle 3.

II. The arm 7 and, therefore, the tool 10 are lowered vertically to puncture the diaphragm, the resulting puncture having a substantially cruciform shape.

III. The arm 7 is raised to remove the tool 10 from the diaphragm. The cruciform puncture closes like a simple valve.

IV. The arm 7 moves to the left relatively to the receptacle 3 by an amount corresponding to the distance between tool 10 and the cannula 9, to bring the cannula into alignment with and concentrically above the receptacle 3.

V. The arm 7 descends to introduce the cannula 9 through the previously produced diaphragm puncture into receptacle 3 and its liquid contents 5, in order to intake liquid.

A number of advantages arise from separating the steps of puncturing the diaphragm and engaging the cannula in the receptacle. The puncturing tool can be of a material and shape such that it requires much less force to puncture the diaphragm. The resulting puncture has an accurate cruciform shape which, if neither the puncturing tool nor the cannula is introduced, immediately recloses substantially sealingly like a valve. Also, the puncture can be so dimensioned due to the action of the shape of the puncturing tool that when the cannula has been introduced there are additional openings enabling pressure equalization with the receptacle interior. Also, the cannula 9 does not need an elaborately sharpened tip. Indeed, the cannula should even be blunt because this has the additional advantage that the cannula fits more accurately into the cylindrical sample injecting channel of a conventional selector or sample input valve with practically no distance to the valve rotor to reduce or virtually eliminate any dead space in which a small liquid volume could otherwise be captioned.

The drive makes no special requirements and can readily be devices by the skilled worker in the manner known from conventional pipetting apparatuses. The only point needing care is to ensure that adjacent receptacles 3 are so disposed in spaced-apart relationship to one another that sufficient space is available for the cannula 9 when the tool 10 is making the puncture and sufficient space is available for the tool 10 during pipetting.

Of course the embodiment described with reference to the drawings merely represents one possible embodiment of the invention modifications are possible. For instance, the invention could be used in pipetting devices having any kind of pivoting arm. Also, the relative lateral movement between, on the one hand, the receptacle 3 and, on the other hand, the cannula and the puncturing tool can be made by means of a receptacle conveyor instead of by moving arm 7.

I claim:

1. An apparatus for withdrawing liquid from a receptacle closed by a penetrable cover, which comprises:
   (a) puncturing tool means for puncturing the receptacle cover;
   (b) cannula means for entering the receptacle through the aperture produced by the puncturing tool means and withdrawing liquid from the receptacle;
   (c) holding arm means to which the puncturing tool means and cannula means are commonly affixed in a parallel side-by-side relationship at a certain distance from one another; and
   (d) driving means for effecting horizontal and vertical movements of the holding arm means relative to the receptacle cover and for aligning the puncturing tool means with the receptacle cover such that in a first of two vertical descents of the holding arm means the puncturing tool means alone pierces the cover, thereby creating a channel, and in a second vertical descent the cannula means penetrates the cover through the channel previously created by the puncturing tool means.

2. The apparatus of claim 1, in which the puncturing tool means has a sharpened tip and is substantially cruciform in cross-sectional shape.

3. An apparatus for withdrawing liquid from a receptacle closed with a penetrable resilient cover, which comprises a horizontally disposed base, a vertically disposed casing affixed to the base and containing a mechanical driving means, a mobile support arm extending at one end laterally from the casing and which is substantially parallel to the base, a hollow pipetting head affixed to the opposite end of the support arm, a puncturing tool rigidly secured to and downwardly extending from the underside of the pipetting head, a cannula rigidly secured to the same underside of the pipetting head which is parellel to and spaced apart from the puncturing tool and is in open communication with a suction means, wherein the driving means is capable of moving the support arm and pipetting head vertically along the length of the casing and horizontally relative to the base.

* * * * *